United States Patent [19]

Nakamura et al.

[11] Patent Number: 5,017,484

[45] Date of Patent: May 21, 1991

[54] PROCESS FOR PREPARING 3-CHLORO-1,2-PROPANEDIOL

[75] Inventors: Yoshio Nakamura, Takasago; Masahiro Ogura, Ono; Yoshio Shimada, Kakogawa; Kiyoshi Watanabe, Akashi; Hideyuki Takahashi, Kakogawa, all of Japan

[73] Assignee: Kanegafuchi Kagaku Kogyo Kabushiki Kaisha, Osaka, Japan

[21] Appl. No.: 933,822

[22] Filed: Nov. 24, 1986

[30] Foreign Application Priority Data

Nov. 25, 1985 [JP] Japan ................................ 60-264567
Nov. 25, 1985 [JP] Japan ................................ 60-264568
Jan. 6, 1986 [JP] Japan ...................................... 61-409
Jul. 31, 1986 [JP] Japan ................................ 61-181164

[51] Int. Cl.$^5$ .......................... C12P 7/18; C12P 7/04; C10N 1/38
[52] U.S. Cl. ..................................... 435/158; 435/280; 435/244; 435/157; 435/822; 435/911
[58] Field of Search ............... 435/158, 157, 280, 244, 435/822, 911

[56] References Cited

U.S. PATENT DOCUMENTS 4,313,008  1/1982  Jones .................................. 568/844

FOREIGN PATENT DOCUMENTS 0060595   9/1982   European Pat. Off.
62-69993  3/1987   Japan.
85/04900  11/1985  World Int. Prop. O.

OTHER PUBLICATIONS

Hasegawa et al., *J. Ferment, Technol.*, 64, pp. 251–254, 1986.
Hohn-Benz et al., *Arch. Microbiol.*, vol. 116, pp. 197–203, 1978.
Sigma Chemial Co., Price list, 1987.
Tang et al., *J. Bacteriology*, vol. 140, 182 (1979).
Wong et al., *J. Org. Chem.* 50, 1992 (1985).
McGregor et al., *J. Biol. Chem.* 249, 3132 Z(1974).
Jones, *Chem. Ind.*, 533 (15 Jul., 1978).
*The Journal of Biological Chemistry*, "D-1-Amino-2-propanol: NAD+ Oxidoreductase", Kelley et al., vol. 259, No. 4, pp. 2124–2129, 1984.

*Primary Examiner*—Douglas W. Robinson
*Assistant Examiner*—Irene Marx
*Attorney, Agent, or Firm*—Armstrong, Nikaido, Marmelstein, Kubovcik & Murray

[57] ABSTRACT

A process for preparing an optically active 3-chloro-1,2-propanediol by employing microorganism which can selectively metabolize (R)- or (S)-3-chloro-1,2-propanediol. The decomposition rate of the substrate can be accelerated and the substrate concentration can be increased by adding a compound having SH group to the reaction solution.

According to the process of the present invention, the optically active 3-chloro-1,2-propanediol can be easily prepared starting from low-cost (R,S)-3-chloro-1,2-propanediol.

6 Claims, No Drawings

PROCESS FOR PREPARING 3-CHLORO-1,2-PROPANEDIOL

BACKGROUND OF THE INVENTION

The present invention relates to a process for preparing an optically active 3-chloro-1,2-propanediol by employing microorganism which can selectively metabolize (R)- or (S)-3-chloro-1,2-propanediol.

The optically active 3-chloro-1,2-propanediol is a useful intermediate for synthesizing a variety of drugs and optically active compounds having physiological activity. For example, (R)-3-chloro-1,2-propanediol have been used for synthesizing L-carnitine (Japanese Unexamined Patent Publication No. 165352/1982).

As the process for preparing (R)-3-chloro-1,2-propanediol, the method employing methyl-5-chloro-5-deoxy-α-L-arabinofuranoside [Hayden F. Jones, Chemistry and Industry, p 538, 15 July, 1978], the method employing 1,2,5,6-diacetonyl-D-mannitol [H. Jackson et al., Chem. -Biol. Interactions, 13, p 193 (1976): Y. Kawakami et al., Journal of Organic Chemistry, 47, p 3581 (1982)]and the like are known.

As the process for preparing (S)-3-chloro-1,2-propanediol, the method employing methyl-6-chloro-6-deoxy-α-D-glucopyranoside (DE Patent No. 2743858), the method employing 1,2,5,6-diacetonyl-D-mannitol [K. E. Porter et al., Chem. -Biol. Interactions, 41, p 95 (1982)]and the like are known.

However, the above processes are not suitable for the industrial production due to disadvantages such as difficulty in obtaining the starting material and complicated steps. Therefore, an industrially advantageous process has been earnestly desired for preparing the optically active 3-chloro-1,2-propanediol.

As a result of the continuous effort of the present inventors to establish an industrial process for preparing the optically active 3-chloro-1,2-propanediol, which hitherto has been prepared by the complicated procedures employing expensive starting materials, it was found that (R)- or (S)-3-chloro-1,2-propanediol can be easily prepared by subjecting low-priced (R,S)-3-chloro-1,2-propanediol to the action of microorganism to selectively metabolizing (S)- or (R)-3-chloro-1,2-propanediol.

SUMMARY OF THE INVENTION

According to the present invention, there are provided a process for preparing (R)-3-chloro-1,2-propanediol, which comprises subjecting (R,S)-3-chloro-1,2-propanediol to the action of microorganism capable of selectively metabolizing (S)-3-chloro-1,2-propanediol, and then collecting the residual (R)-3-chloro-1,2-propanediol, and a process for preparing (S)-3-chloro-1,2-propanediol which comprises subjecting (R,S)-3-chloro-1,2-propanediol to the action of microorganism capable of selectively metabolizing (R)-3-chloro-1,2-propanediol, and then collecting the residual (S)-3-chloro-1,2-propanediol,

DETAILED DESCRIPTION

For the microorganism capable of selectively metabolizing (S)-3-chloro-1,2-propanediol, microorganisms of the genus selected from the group consisting of Depodascus, Sporidiobolus, Geotrichum, Hansenula, Lodderomyces, Kluyveromyces, Nadsonia, Pichia, Saccharomyces, Saccharomycopsis, Rhodosporidium, Rhodotorula, Wickerhamia, Candida, Stephanoascus, Pachysolen, Schizosaccharomyces, Sporobolomyces, Brettanomyces, Escherichia, Aeromonas, Acidiphilium, Micrococcus, Bacillus, Enterobacter, Nocardia, Protaminobacter, Pseudomonas, Pemelobocter, Hafnia, Klebsiella, Rhodococcus, Gluconobacter, Absidia, Amauroascus, Anixiopsis, Ascosphaera, Aspergillus, Acremoniella, Acrodontium, Arxiella, Cladosporium, Beauveria, Calonectria, Coniochaetidium, Backusella, Beltraniella, Cladobotryum, Chloridium, Corticium, Cunninghamella, Circinella, Botryoconis, Emericella, Gliocladium, Gliocephalotrichum, Helicosporium, Melanospora, Micronectriella, Echinopodospora, Gliomastix, Gelasinospora, Deightoniella, Dendryphiella, Dichotomomyces, Mortierella, Pycnoporus, Sporormiella, Syncephalastrum, Talaromyces, Pellicularia, Neosartorya, Penicillium, Thamnostylum, Zygorhynchus, Monascus and Periconia are employed.

More particularly, microorganisms such as *Depodascus magnusii* CBS 164.32, *Sporidiobolus johnsonii* IFO 6903, *Geotrichum candidum* CBS 187.67, *Hansenula anomala* IFO 0707, *Lodderomyces elongisporus* IFO 1676, *Kluyveromyces fragilis* IAM 4763, *Nadsonia elongata* IFO 0665, *Pichia burtonii* IFO 0844, *Saccharomyces cerevisiae* IFO 0267, *Saccharomycopsis lypolytica* IFO 0717, *Rhodosporidium toruloides* IFO 0871, *Rhodotorula rubra* IFO 0383, *Wickerhamia fluorescens* IFO 1116, *Candida humicola* CBS 2774, *Candida utilis* IFO 0626, *Stephanoascus ciferrii* IFO 1854, *Candida gropengiesseri* IFO 0659, *Pachsolen tannophilus* IFO 1007, *Schizosaccharomyces pombe* IFO 0362, *Sporobolomyces salmonicolor* IAM 12249, *Brettanomyces custersianus* IFO 1585, *Escherichia coli* IFO 12734, *Aeromonas hydrophila* IFO 3820, *Acidiphilium cryptum* IFO 14242, *Micrococcus luteus* IFO 12708, *Bacillus cereus* IFO 3001, *Enterobacter aerogenes* IFO 13534, *Nocardia globerula* IFO 13510, *Protaminobacter alboflavus* IFO 3707, *Pseudomonas fragi* IFO 3458, *Pseudomonas cruciviae* IFO 12047, *Pseudomonas chlororaphis* IFO 3904, *Pemelobacter simplex* IFO 12069, *Hafnia alvei* IFO 3731, *Klebsiella pneumoniae* IFO 12009, *Rhodococcus erythropolis* IFO 12320, *Gluconobacter suboxydans* IFO 3254, *Absidia corymbifera* IFO 4009, *Amauroascus reticulatus* IFO 9196, *Anixiopsis fulvescens* IFO 30411, *Ascosphaera apis* IFO 9831, *Aspergillus ficuum* IFO 4034, *Acremoniella atra* IFO 5937, *Acrodontium crateriforme* IFO 30442, *Arxiella terrestris* IFO 30203, *Cladosporium resinae* IFO 6367, *Beauveria bassiana* IFO 8554, *Calonectria hederae* IFO 30427, *Coniochaetidium savoryi* IFO 30424, *Backusella circina* IFO 9231, *Beltraniella japonica* IFO 30443, *Cladobotryum apiculatum* IFO 7795, *Chloridium chlamydosporis* IFO 7070, *Corticium rolfsii* IFO 30071, *Cunninghamella echinulata* IFO 4441, *Circinella simplex* IFO 6412, *Botryoconis japonica* IFO 4862, *Emericella nidulans* IFO 4340, *Gliocladium deliquescens* IFO 6790, *Gliocephalotrichum cylindosporum* IFO 9326, *Helicosporium linderi* IFO 9207, *Melanospora ornata* IFO 8354, *Micronectriella cucumeris* IFO 30005, *Echinopodospora jamaicensis* IFO 30406, *Gliomastix murorum* IFO 8269, *Gelasinospora cerealis* IFO 6759, *Deightoniella torulosa* IFO 7658, *Dendryphiella salina* IFO 8281, *Dichotomomyces cejpii* IFO 8396, *Mortierella humicola* IFO 8188, *Pycnoporus coccineus* IFO 9768, *Sporormiella isomera* IFO 8538, *Syncephalastrum nigricans* HUT 1299, *Talaromyces flavus* IFO 7231, *Pellicularia filamentosa* IFO 6254, *Neosartorya aurata* IFO 8783, *Penicillium janthinellum* IFO 4651, *Thamnostylum piriforme* IFO 6117, *Zygorhynchus moelleri* HUT 1305, *Monascus anka*

IFO 5965 and *Periconia byssoides* IFO 9444 are employed.

For the microorganism capable of selectively metabolizing (R)-3-chloro-1,2-propanediol, micoorganisms of the genus selected from the group consisting of Geotrichum, Pichia, Corynebacterium and Morganella are employed.

More particularly, microorganisms such as *Geotrichum fermentans* CBS 2264, *Pichia farinosa* IFO 1003, *Corynebacterium acetoacidophilum* ATCC 21476 and *Morganella morganii* IFO 3168 are employed.

Further, as a result of the present inventors' continuous effort to increase the production rate in the process for preparing optically active 3-chloro-1,2-propanediol by employing the microorganism, it was found that the decomposition rate of the substrate can be accelerated and the substrate concentration can be increased by adding a compound having SH group to the reaction solution.

Examples of the compound having SH group which can be employed in the present invention are, for instance, dithiothreitol, dithioerythritol, glutathione, cysteine, mercaptoethanol, thioglycerol, 2,3-dimercaptopropanol, thioacetic acid, dimercaptosuccinic acid, 2-mercaptopropionic acid, 3-mercaptopropionic acid, thioglycollic acid, tert-butyl mercaptan, sodium hydrosulfide, potassium hydrosulfide and the like.

When the residual optically active 3-chloro-1,2-propanediol is (R)-form, microorganisms of the genus selected from the group consisting of Brettanomyces, Candida, Dipodascus, Geotrichum, Kluyveromyces, Nadsonia, Pachysolen, Rhodosporidium, Saccharomyces, Sporidiobolus, Torulopsis, Bacillus, Enterobacter, Escherichia, Klebsiella, Pinelobacter, Aspergillus, Beauveria, Calonectoria, Conichaetidium, Backusella, Cladobotryum, Chloridium, Corticium, Cunninghamella, Cirlinella, Gliocladium, Gliocephalotrichum, Echinopodospora, Gelasinospora, Dichotomomyces, Pycnoporus, Neosartorya, Penicillium, Thamnostylum, Zygorhynchus and Monascus are employed.

More particularly, microorganisms such as *Brettanomyces custerisianus* IFO 1585, *Candida utilis* IFO 0626, *Dipodascus magnusii* CBS 164.32, *Geotrichum candidum* CBS 187.67, *Kluyveromyces fragilis* IAM 4763, *Nadsonia elongata* IFO 0665, *Pachysolen tannophilus* IFO 1007, *Rhodosporidium toruloides* IFO 0871, *Saccharomycopsis lipolytica* IFO 0717, *Sporidiobolus johnsonii* IFO 6903, *Candida gropengiesseri* IFO 0659, *Bacillus cereus* IFO 3001, *Enterobacter aerogenes* IFO 13534, *Escherichia coli* IFO 12734, *Klebsiella pneumoniae* IFO 12009, *Pimelobacter simplex* IFO 12069, *Aspergillus ficuum* IFO 4034, *Beaveria bassiana* IFO 8554, *Calonectria hederae*, *Conichaetidium savoryi* IFO 30424, *Backusella circina* IFO 9231, *Cladobotryum apiculatum* IFO 7795, *Chloridium chlamydosporis* IFO 7070, *Corticium rolfsii* IFO 30071, *Cunninghamella echinulata* IFO 4441, *Circinella simplex* IFO 6412, *Gliocladium deliquescens* IFO 6790, *Gliocephalotrichum cylindrosporum* IFO 9326, *Echinopodospora jamaicensis* IFO 30406, *Gelasinospora cerealis* IFO 6759, *Dichotomomyces cejpii* IFO 8396, *Pycnoporus coccineus* IFO 9768, *Neosartorya aurata* IFO 8783, *Penicillium janthinellum* IFO 4651, *Thamnostylum piriforme* IFO 6117, *Zygorhynchus moelleri* HUT 1305 and *Monascus anka* IFO 5965 are employed.

When the residual optically active 3-chloro-1,2-propanediol is (S)-form, microorganisms of the genus selected from the group consisting of Pichia, Geotrichum, and Corynebacterium are employed. More particularly, microorganisms such as *Pichia farinosa* IFO 1003, *Trichosporon fermentans* CBS 2264 and *Corynebacterium acetoacidophilum* ATCC 21476 are employed.

As the culture medium for culturing the above-mentioned microorganisms, any culture medium can be employed where these microorganisms can usually grow. The culture medium may optionally contain nutrient sources which are employed in the usual culture, for example, sugars such as glucose, sucrose and maltose, alcohols such as ethanol, glycerol and 1,2-propanediol, organic acids such as acetic acid and lactic acid, or the mixture thereof as a carbon source, ammonium sulfate, ammonium phosphate, urea, yeast extract, meat extract or peptone as a nitrogen source, an inorganic salt, trace amounts of metal salt, vitamin and the like.

The microorganisms as mentioned above are cultured in the conventional manner. For example, the microorganisms are preferably cultured in the culture medium of pH ranging from 4.0 to 9.5 at a temperature of from 20° to 45° C. for 10 to 96 hours under the aerobic condition.

(R,S)-3-Chloro-1,2-propanediol is subjected to the action of the microorganism to prepare optically active 3-chloro-1,2-propanediol, by adding the substrate to a culture solution cultured as mentioned above or to a suspension of the cells obtained by a centrifugation, by adding the substrate to the culture medium to conduct the culture and the reaction concurrently, or by adding the substrate to a suspension of the immobilized microorganism in a suitable buffer.

The reaction is preferably carried out at a temperature of from 15° to 50° C. at a pH of from 4.0 to 10.0. For obtaining a constant pH value, suitable buffer and the like can be employed.

The substrate concentration in the reaction solution is preferably 0.1 to 10 % (w/v). The substrate may be added to the reaction solution either at a stretch or in portions.

When the reaction is conducted, the reaction rate can be accelerated by adding the compound having SH group to the reaction solution. The concentration of the compound having SH group in the reaction solution is preferably 0.05 to 10 % (w/v). The compound may be added to the reaction solution either continuously or in portions.

The reaction is usually carried out with shaking or stirring. Although the reaction time may vary depending on the reaction condition such as the substrate concentration or the amount of the enzyme, the reaction condition is preferably selected so that the reaction is completed within 72 hours.

In the progress of the reaction, the residual substrate is monitored by a gas chromatography or the like and the reaction is preferably stopped when around 50 % of the substrate is consumed for obtaining a high yield.

The thus prepared optically active 3-chloro-1,2-propanediol can be collected from the reaction solution by the method usually employed for the collection of 3-chloro-1,2-propanediol. For example, after removing the cells from the reaction solution by centrifugation and the like, the supernatant is suitably concetrated and the concentrate is extracted with a solvent such as ethyl acetate. After dehydrating the extract with anhydrous sodium sulfate and the like, the solvent is removed under reduced pressure to give a syrup of optically active 3-chloro-1,2-propanediol, which may be further purified by distillation.

The present invention id described and explained in more detail by means of the following Examples. However, it should be understood that the present invention is not limited to such Examples and various changes and modifications can be made without departing from the scope of the present invention.

EXAMPLES 1 TO 41

A culture medium containing 4 % of glucose, 1.3 % of $(NH_4)_2HPO_4$, 0.7 % of $KH_2PO_4$, 800 ppm of $MgSO_4 \cdot 7H_2O$, 60 ppm of $ZnSO_4 \cdot 7H_2O$, 90 ppm of $FeSO_4 \cdot 7H_2O$, 5 ppm of $CuSO_4 \cdot 5H_2O$, 10 ppm of $MnSO_4 \cdot 4H_2O$, 100 ppm of NaCl and 0.3 % of yeast extract was prepared with deionized water (pH 7.0). Each 2 l Sakaguchi flask charged with 500 ml of the culture medium was sterilized at 120° C. for 20 minutes.

Each microorganism shown in Table 1 was inoculated into the above culture medium and the shaking culture was conducted at 30° C. for 48 hours to give 1.5 l of the culture solution. The cells were collected by the centrifugation of the culture solution and was washed with water. To a suspension of the cells in 500 ml of 0.3 phosphate buffer (pH 7.0) was added 2 g of (R,S)-3-chloro-1,2-propanediol to conduct the reaction at 30° C. for 72 hours with shaking.

After removing the cells from 500 ml of the reaction solution by the centrifugation, the supernatant was concentrated to about 50 ml and was extracted three times with ethyl acetate (150 ml×3). The extract was dehydrated with anhydrous sodium sulfate and then the solvent was removed under reduced pressure to give a syrup.

Specific rotatory power of the syrup was measured to give the values as shown in Table 1.

Literature value of (R)-3-chloro-1,2-propanediol: $[\alpha]^{22}_D - 6.9$ (c=2,$H_2O$)
Literature value of (S)-3-chloro-1,2-propanediol: $[\alpha]^{20}_D + 7.3$ (c=1, $H_2O$)

After tosylating each syrup in the conventional manner, HPLC analysis was conducted with the chiral column [CHIRALCELL O.C (0.46 cm×25 cm) made by Japan Spectroscopic] by employing a mixed solvent (hexane: isopropyl alcohol 95:5) at a flow rate of 2.0 ml/min and a wave length of 235 nm. The analysis confirmed that each syrup contained the corresponding (R)-form or (S)-form.

TABLE 1

| Ex. | Microorganism | Yield (%) | Specific rotatory power $[\alpha]_D^{20}$ (c = 2, $H_2O$) |
|---|---|---|---|
| 1 | Dipodascus magnusii CBS 164.32 | 24 | −4.04 |
| 2 | Sporidiobolus johnsonii IFO 6903 | 26 | −7.25 |
| 3 | Geotrichum candidum CBS 187.67 | 27 | −6.20 |
| 4 | Hansenula anomala IFO 0707 | 32 | −5.33 |
| 5 | Lodderomyces elongisporus IFO 1676 | 29 | −4.43 |
| 6 | Kluyveromyces fragilis IAM 4763 | 22 | −7.19 |
| 7 | Nadsonia elongata IFO 0665 | 35 | −7.27 |
| 8 | Pichia burtonii IFO 0844 | 28 | −4.95 |
| 9 | Saccharomyces cerevisiae IFO 0267 | 36 | −5.45 |
| 10 | Saccharomycopsis lypolytica IFO 0717 | 28 | −5.80 |
| 11 | Rhodosporidium toruloides IFO 0871 | 13 | −4.13 |
| 12 | Rhodotorula rubra IFO 0383 | 31 | −5.43 |
| 13 | Wickerhamia fluorescens IFO 1116 | 32 | −6.98 |
| 14 | Candida humicola CBS 2774 | 36 | −6.53 |
| 15 | Candida utilis IFO 0626 | 25 | −5.87 |
| 16 | Stephanoascus ciferrii IFO 1854 | 45 | −3.64 |
| 17 | Candida gropengiesseri IFO 0659 | 27 | −8.02 |
| 18 | Pachysolen tannophilus IFO 1007 | 10 | −4.95 |
| 19 | Schizosaccharomyces pombe IFO 0362 | 29 | −8.11 |
| 20 | Sporobolomyces salmonicolor IAM 12249 | 28 | −8.17 |
| 21 | Brettanomyces custersianus IFO 1585 | 31 | −5.36 |
| 22 | Escherichia coli IFO 12734 | 37 | −5.39 |
| 23 | Aeromonas hydrophila IFO 3820 | 32 | −3.56 |
| 24 | Acidiphilium cryptum IFO 14242 | 42 | −4.53 |
| 25 | Micrococcus luteus IFO 12708 | 32 | −4.79 |
| 26 | Bacillus cereus IFO 3001 | 37 | −4.10 |
| 27 | Enterobacter aerogenes IFO 13534 | 33 | −4.50 |
| 28 | Nocardia globerula IFO 13510 | 31 | −3.54 |
| 29 | Protaminobacter alboflavus IFO 3707 | 38 | −7.49 |
| 30 | Pseudomonas fragi IFO 3458 | 35 | −7.14 |
| 31 | Pseudomonas cruciviae IFO 12047 | 39 | −6.48 |
| 32 | Pseudomonas chlororaphis IFO 3904 | 24 | −5.12 |
| 33 | Pimelobacter simplex IFO 12069 | 22 | −3.64 |
| 34 | Hafnia alvei IFO 3731 | 21 | −7.80 |
| 35 | Klebsiella pneumonias IFO 12009 | 30 | −6.00 |
| 36 | Rhodococcus erythropolis IFO 12320 | 44 | −3.36 |
| 37 | Gluconobacter suboxydans IFO 3254 | 35 | −5.60 |
| 38 | Geotrichum fermentans | 32 | +3.40 |

TABLE 1-continued

| Ex. | Microorganism | Yield (%) | Specific rotatory power $[\alpha]_D^{20}$ (c = 2, H$_2$O) |
|---|---|---|---|
|  | CBS 2264 |  |  |
| 39 | Pichia farinosa IFO 1003 | 30 | +4.02 |
| 40 | Corynebacterium acetoacidophilum ATCC 21476 | 37 | +7.47 |
| 41 | Morganella monganii IFO 3168 | 39 | +5.18 |

The obtained yield was based on (R,S)-3-chloro-1,2-propanediol.

In Example 37, however, the culture medium containing 2% of glucose, 2% of glycerol, 2% of corn steep liquor, 0.3% of yeast extract and 1% of calcium carbonate was employed in place of the above culture medium.

EXAMPLES 42 to 85

A culture medium containing 2% of glucose, 1% of peptone, 1% of meat extract, 0.5% of yeast extract and 0.1% of NaCl was prepared with deionized water (pH 6.5). Each 2 l Sakaguchi flask charged with 500 ml of the culture medium was sterilized at 120° C. for 20 minutes.

Each microorganism shown in Table 2 was inoculated into the above culture medium and the shaking culture was conducted at 30° C. for 48 hours to give 1 l of the culture solution. The cells were collected by the centrifugation of the culture solution and were washed with water. To a suspension of the cells in 500 ml of 0.3 M phosphate buffer (pH 7.0) was added 1.5 g of (R,S)-3-chloro-1,2-propanediol to conduct the reaction at 30° C. for 96 hours with shaking.

After removing the cells from 500 ml of the reaction solution by the centrifugation, the supernatant was concentrated to about 50 ml and was extracted three times with ethyl acetate (150 ml×3). The extract was dehydrated with anhydrous sodium sulfate and then the solvent was removed under reduced pressure to give a syrup.

Specific rotatory power of the syrup was measured to give the values as shown in Table 2.

TABLE 2

| Ex. | Microorganism | Yield (%) | Specific rotatory power $[\alpha]_D^{20}$ (c = 2, H$_2$O) |
|---|---|---|---|
| 42 | Absidia corymbifera IFO 4009 | 35 | −5.01 |
| 43 | Amauroascus reticulatus IFO 9196 | 32 | −8.11 |
| 44 | Anixiopsis fulvescens IFO 30411 | 37 | −6.91 |
| 45 | Ascosphaera apis IFO 9831 | 36 | −4.63 |
| 46 | Aspergillus ficuum IFO 4034 | 33 | −5.23 |
| 47 | Acremoniella atra IFO 5937 | 40 | −4.37 |
| 48 | Acrodontium crateriforme IFO 30442 | 20 | −4.04 |
| 49 | Arxiella terrestis IFO 30203 | 38 | −4.93 |
| 50 | Cladosporium resinae IFO 6367 | 21 | −8.63 |

TABLE 2-continued

| Ex. | Microorganism | Yield (%) | Specific rotatory power $[\alpha]_D^{20}$ (c = 2, H$_2$O) |
|---|---|---|---|
| 51 | Beauveria bassiana IFO 8554 | 33 | −5.70 |
| 52 | Calonectria hederae IFO 30427 | 39 | −4.05 |
| 53 | Coniochaetidium savoryi IFO 30424 | 31 | −7.32 |
| 54 | Backusella circina IFO 9231 | 38 | −6.40 |
| 55 | Beltraniella japonica IFO 30443 | 37 | −4.86 |
| 56 | Cladobotryum apiculatum IFO 7795 | 33 | −8.38 |
| 57 | Chloridium chlamydosporis IFO 7070 | 32 | −6.45 |
| 58 | Corticium rolfsii IFO 30071 | 44 | −3.68 |
| 59 | Cunninghamella echinulata IFO 4441 | 47 | −7.74 |
| 60 | Circinella simplex IFO 6412 | 30 | −5.28 |
| 61 | Botryoconis japonica IFO 4862 | 38 | −4.76 |
| 62 | Emericella nidulans IFO 4340 | 28 | −5.58 |
| 63 | Gliocladium deliquescens IFO 6790 | 26 | −4.90 |
| 64 | Gliocephalotrichum cylindosporum IFO 9326 | 26 | −5.25 |
| 65 | Helicosporium linderi IFO 9207 | 42 | −4.72 |
| 66 | Melanospora ornata IFO 8354 | 46 | −4.25 |
| 67 | Micronectriella cucumeris IFO 30005 | 30 | −7.51 |
| 68 | Echinopodospora jamaicensis IFO 30406 | 34 | −8.04 |
| 69 | Gliomastix murorum IFO 8269 | 32 | −6.44 |
| 70 | Gelasinospora cerealis IFO 6759 | 43 | −6.32 |
| 71 | Deightoniella torulosa IFO 7658 | 36 | −6.36 |
| 72 | Dendryphiella salina IFO 8281 | 34 | −5.40 |
| 73 | Dichotomomyces cejpii IFO 8396 | 35 | −3.33 |
| 74 | Mortierella humicola IFO 8188 | 39 | −4.73 |
| 75 | Pycnoporus coccineus IFO 9768 | 27 | −6.12 |
| 76 | Sporormiella isomera IFO 8538 | 22 | −3.78 |
| 77 | Syncephalastrum nigricans HUT 1299 | 35 | −4.43 |
| 78 | Talaromyces flavus IFO 7231 | 35 | −6.63 |
| 79 | Pellicularia | 29 | −3.45 |

TABLE 2-continued

| Ex. | Microorganism | Yield (%) | Specific rotatory power $[\alpha]_D^{20}$ (c = 2, H$_2$O) |
|---|---|---|---|
|  | filamentosa IFO 6254 |  |  |
| 80 | Neosartorya aurata IFO 8783 | 38 | −5.98 |
| 81 | Penicillium janthinellum IFO 4651 | 40 | −5.84 |
| 82 | Thamnostylum piriforme IFO 6117 | 30 | −5.34 |
| 83 | Zygorhynchus moelleri HUT 1305 | 38 | −5.24 |
| 84 | Monascus anka IFO 5965 | 39 | −5.67 |
| 85 | Periconia byssoides IFO 9444 | 22 | −3.90 |

EXAMPLE 86

A culture medium containing 4% of glycerol, 1.3% of (NH$_4$)$_2$HPO$_4$, 0.7% of KH$_2$PO$_4$, 800 ppm of MgSO$_4$·7H$_2$O, 60 ppm of ZNSO$_4$·7H$_2$O, 90 ppm of FeSO$_4$·7H$_2$O, 5 ppm of CuSO$_4$·5H$_2$O, 10 ppm of MnSO$_4$·4H$_2$O, 100 ppm of NaCl and 0.3% of yeast extract was prepared with deionized water (pH 7.00. Each 500 ml Sakaguchi flask charged with 50 ml of the culture medium was sterilized at 120° C. for 20 minutes.

*Saccharomycopsis lipolytica* IFO 0717 was inoculated into the above culture medium and the shaking culture was conducted at 30° C. for 48 hours to give 150 ml of the culture solution. The cells were collected by the centrifugation of the culture solution and were washed with water. To a suspension of the cells in 50 ml of 0.3 M phosphate buffer (pH 7.0) were added 0.5 g of (R,S)-3-chloro-1,2-propanediol and each 0.15 g of the compounds having SH group shown in Table 3 to conduct the reaction at 30° C. for 24 hours with shaking.

One milliliter of the reaction solution was subjected to the extraction with 2 ml of ethyl acetate and the extract was analyzed with a gas chromatography to examine the decomposition rate of the substrate.

Column length: 50 cm
Filler: FAL-M 6%
    support: TENAX GC (made by SHIMADZU CORPORATION
Carrier gas: N$_2$ (22.5 ml/min.)
Column temperature: 175° C.
Detection: FID
Retention time 1.8 min. (3-chloro-1,2-propanediol)

Table 3 shows an effect of various compounds having SH group on the decomposition rate of the substrate.

TABLE 3

| Compound having SH group | Decomposition rate of the substrate (after 24 hours) (%) | Degree of the effect* |
|---|---|---|
| (Control) | 22 | — |
| Dithiothreitol | 40 | 1.82 |
| Dithioerythritol | 41 | 1.86 |
| Glutathione | 39 | 1.77 |
| Cysteine | 38 | 1.73 |
| Mercaptoethanol | 36 | 2.64 |
| Thioglycerol | 48 | 2.18 |
| 2,3-Dimercaptopropanol | 38 | 1.73 |
| Thioacetic acid | 42 | 1.91 |
| Dimercaptosuccinic acid | 41 | 1.86 |
| 2-Mercaptopropionic acid | 38 | 1.73 |
| 3-Mercaptopropionic acid | 36 | 1.64 |
| Thioglycollic acid | 39 | 1.77 |
| tert-Butyl mercaptan | 34 | 1.55 |
| Sodium hydrosulfide | 41 | 1.86 |
| Potassium hydrosulfide | 44 | 2.00 |

(Note)*

$$\text{Degree of the effect} = \frac{\text{Decomposition rate when the compound is added (after 24 hours)}}{\text{Decomposition rate in control (after 24 hours)}}$$

In the case of the addition of thioglycerol or potassium hydrosulfide, which showed especially high effect, the purification was conducted in the following manner.

After removing the cells from the reaction solution by centrifugation, the supernatant was concentrated to about 10 ml and was extracted three times with ethyl acetate (30 ml×3). The extract was dehydrated with anhydrous sodium sulfate and then the solvent was removed under reduced pressure to give a syrup. After distillation of the syrup, specific rotatory power was measured to give the following values.

Addition of thioglycerol:
    $[\alpha]^{20}_D = -5.23°$ (c=2.0, H$_2$O)
Addition of sodium hydrosulfide:
    $[\alpha]^{20}_D = -5.35°$ (c=2.0, H$_2$O)
Literature value of (R)-3-chloro-1,2-propanediol:
    $[\alpha]^{20}_D = -6.9°$ (c=2, H$_2$O)

The above results show that the addition of the compound having SH group does not affect the discrimination of the optical activity and (R)-3-chloro-1,2-propanediol can be obtained in the same manner as in the case of control.

EXAMPLES 87 TO 125

The procedure in Example 86 was repeated except that microorganisms shown in Table 4 were employed to give the results as shown in Table 4. As the compound having SH group, thioglycerol was employed. In Examples 102 to 122, however, glucose was employed as a carbon source in the culture medium in place of glycerol.

TABLE 4

| | | Decomposition rate of the substrate (after 24 hours) | | |
|---|---|---|---|---|
| Ex. | Microorganism | Control (%) | With addition of the SH compound (%) | Degree of the effect |
| 87 | Brettanomyces custersianus IFO 1585 | 17 | 31 | 1.82 |
| 88 | Candida utilis IFO 0626 | 21 | 37 | 1.76 |
| 89 | Dipodascus magnusii CBS 164.32 | 14 | 28 | 2.00 |
| 90 | Geotrichum candidum CBS 187.67 | 23 | 38 | 1.65 |
| 91 | Kluyveromyces fragilis IAM 4763 | 18 | 31 | 1.72 |
| 92 | Nadsonia elongata | 26 | 44 | 1.69 |

TABLE 4-continued

| Ex. | Microorganism | Decomposition rate of the substrate (after 24 hours) Control (%) | Decomposition rate of the substrate (after 24 hours) With addition of the SH compound (%) | Degree of the effect |
|---|---|---|---|---|
| 93 | Pachysolen tannophilus IFO 1007 | 25 | 37 | 1.48 |
| 94 | Rhodosporidium toruloides IFO 0871 | 12 | 28 | 2.33 |
| 95 | Sporidiobolus johnsonii IFO 6903 | 26 | 39 | 1.50 |
| 96 | Candida gropengiesseri IFO 0659 | 10 | 21 | 2.10 |
| 97 | Bacillus cereus IFO 3001 | 34 | 55 | 1.62 |
| 98 | Enterobacter aerogenes IFO 13534 | 39 | 51 | 1.31 |
| 99 | Escherichia coli IFO 12734 | 23 | 37 | 1.61 |
| 100 | Klebsiella pneumoniae IFO 12009 | 27 | 58 | 2.15 |
| 101 | Pimelobacter simplex IFO 12069 | 28 | 49 | 1.75 |
| 102 | Aspergillus ficuum IFO 4034 | 25 | 38 | 1.52 |
| 103 | Beauveria bassiana IFO 8554 | 37 | 55 | 1.49 |
| 104 | Calonectria hederae IFO 30427 | 26 | 43 | 1.65 |
| 105 | Conichaetidium savoryi IFO 30424 | 23 | 53 | 2.30 |
| 106 | Backusella circina IFO 9231 | 18 | 38 | 2.11 |
| 107 | Cladobotryum apiculatum IFO 7795 | 22 | 46 | 2.09 |
| 108 | Chloridium clamydosporis IFO 7070 | 37 | 57 | 1.54 |
| 109 | Corticium rolfsii IFO 30071 | 18 | 33 | 1.83 |
| 110 | Cunninghamella echinulata IFO 4441 | 26 | 44 | 1.69 |
| 111 | Circinella simplex IFO 6412 | 16 | 27 | 1.69 |
| 112 | Gliocladium deliquescens IFO 6790 | 24 | 43 | 1.79 |
| 113 | Gliocephalotrichum cylindrosporum IFO 9326 | 20 | 30 | 1.50 |
| 114 | Echinopodospora jamaicensis IFO 30406 | 23 | 36 | 1.57 |
| 115 | Gelasinospora cerealis IFO 6759 | 25 | 37 | 1.48 |
| 116 | Dichotomyces cejpii IFO 8396 | 21 | 36 | 1.71 |
| 117 | Pycnoporus coccineus IFO 9768 | 16 | 31 | 1.94 |
| 118 | Neosartorya aurata IFO 8783 | 21 | 38 | 1.81 |
| 119 | Penicillium janthinellum IFO 4651 | 30 | 42 | 1.40 |
| 120 | Thamnostylum piriforme IFO 6117 | 26 | 38 | 1.46 |
| 121 | Zygorhynchus moelleri HUT 1305 | 33 | 52 | 1.58 |
| 122 | Monascus ancha IFO 5965 | 22 | 37 | 1.68 |
| 123 | Pichia farinosa IFO 1003 | 21 | 42 | 2.00 |
| 124 | Geotrichum fermentans CBS 2264 | 30 | 41 | 1.37 |
| 125 | Corynebacterium acetoacidophilum ATCC 21476 | 19 | 36 | 1.89 |

(Note)
Examples 87 to 122: Microorganism accumulating (R)-form
Examples 123 to 125: Microorganism accumulating (S)-form The reaction solution in Example 105 (Conichaetidium savoryi IFO 30424) was subjected to the extraction and purification procedure as in Example 86 and specific rotatory power was measured.

$[\alpha]^{20}_D = -7.28°$ (c=2.0, H$_2$O)

What we claim is:

1. A process for preparing (R)-3-chloro-1,2-propanediol, which comprises subjecting (R,S)-3-chloro-1,2-propanediol to the action of microorganism capable of selectively metabolizing (S)-3-chloro-1,2-propanediol, and then collecting the residual (R)-3-chloro-1,2-propanediol, wherein the microorgansim is selected from the group consisting of Dipodascus magnusiii CBS 164.32, Sporidiobolus johnsonii IFO 6903, Geotrichum candidum CBS 187.67, Hansenula anomala IFO 0707, Lodderomyces elongisporus IFO 1676, Kluyveromyces fragilis IAM 4763, Nadsonia elongata IFO 0665, Pichia burtonii IFO 0844, Saccharomyces cerevisiae IFO 0267, Saccharomycopsis lipolytica IFO 0717, Rhodosporidium toruloides IFO 0871, Rhodotorula rubra IFO 0383, Wickerhamia fluorescens IFO 1116, Candida humicola CBS 2774, Candida utilis IFO 0626, Stephanoascus ciferrii IFO 1854, Candida Gropengiesseri IFO 0659, Pachysolen tannophilus IFO 1007, Schizosaccharomyces pombe IFO 0362, Sporobolomyces salmonicolor IAM 12249, Brettanomyces custersianus IFO 1585, Escherichia coli IFO 12734, Aeromonas hydrophila IFO 3820, Acidiphilium cryptum IFO 14242, Micrococcus luteus IFO 12708, Bacillus cereus IFO 3001, Enterobacter aerogenes IFO 13534, Nocardia globerula IFO 13510, Protaminobacter alboflavus IFO 3707, Pseudomonas fragi IFO 3458, Pseudomonas cruciviae IFO 12047, Pseudomonas chlororaphis IFO 3904, Pimelobacter simplex IFO 12069, Hafnia alvei IFO 3731, Klebsiella pneumoniae IFO 12009, *Rhodococcus erythropolis* IFO 12320, *Gluconobacter suboxydans* IFO 3254, *Absidia corymbifera* IFO 4009, *Amauroascus reticulatus* IFO 9196, *Anixiopsis fulvescens* IFO 30411, *Ascosphaera apis* IFO 9831, *Aspergillus ficuum* IFO 4034, *Acremoniella atra* IFO 5937, *Acrodontium crateriforme* IFO 30442, *Arxiella terestris* IFO 30203, *Cladosporium resinae* IFO 6367, *Beauveria bassiana* IFO 8554, *Calonectria hederae* IFO 30427, *Coniochaetidium savoryi* IFO 30424, *Backusella circina* IFO 9231, *Beltraniella japonica* IFO 30443, *Cladobotryum apiculatrum* IFO 7795, *Chloridium chlamydosporis* IFO 7070, *Corticium rolfsii* IFO 30071, *Cunninghamella echinulata* IFO 441, *Circinella simplex* IFO 6412 *Botryoconis japonica* IFO 4862, *Emericella nidulans* IFO 4340, *Gliocladium deliquescens* IFO 6790, *Gliocephalotrichum cylindosporum* IFO 9326, *Helicosporium linderi* IFO 9207, *Melanospora ornata* IFO 8354, *Micronectriella cucumeris* IFO 30005, *Echinopodospora jamaicensis* IFO 30406, *Gliomastrix murrorum* IFO 8269, *Gelasinosipora cerealis* IFO 6759, *Deightoniella torulosa* IFO 7658, *Dendryphiella salina* IFO 8281, *Dichotomomyces cejpii* IFO 8396, *Mortierella humicola* IFO 8188, *Pycnoporus coccineus* IFO 9768, *Sporormiella isomera* IFO 8538, *Syncephalastrum nigricans* HUT 1299, *Talaromyces flavus* IFO 7231, *Pellicularia felamentosa* IFO 6254, *Neosartorya aurata* IFO 8783, *Penicillium janthinellum* IFO 4651, *Thamnostylum piriforme* IFO 6117, *Zygorhynchus moelleri* HUT 1305, *Monascus anka* IFO 5965 and *Periconia byssoides* IFO 9444.

2. A process for preparing (S)-3-chloro-1,2-propanediol, which comprises subjecting (R,S)-3-chloro-1,2-propanediol to the action of a microorganism capable of selectively metabolizing (R)-3-chloro-1,2-propanediol, and then collecting the residual (S)-3-chloro-1,2-propanediol, wherein the microorganism is selected from the group consisting of *Geotrichum fermentans* CBS 2264, *Pichia farinosa* IFO 1003, *Corynebacterium acetoacidophilum* ATCC 21476 and *Morganella morganii* IFO 3168.

3. A process for preparing optically active 3-chloro-1,2-propanediol, which comprises subjecting (R,S)-3-chloro-1,2-propanediol to the action of a microorganism capable of selectively metabolizing (S)-3-chloro-1,2-propanediol, wherein a compound having an SH group is added to the reaction solution, and collecting the residual (R)-3-chloro-1,2-propanediol and the microorganism is selected from the group consisting of *Brettanomyces custersianus* IFO 1585, *Candida utilis* IFO 0602, *Dipodascus magnusii* CBS 164.32, *Geotrichum candidum* CBS 187.67, *Kluyveromyces fragilis* IAM 4763, *Nadsonia elongata* IFO 0665, *Pachysolen tannophilus* IFO 1007, *Rhodosporidium toruloides* IFO 0871, *Saccharomycopsis lipolytica* IFO 0717, *Sporidiobolus johnsonii* IFO 6903, *Candida gropengiesseri* IFO 0659, *Bacillus cereus* IFO 3001, *Enterobacter aerogenes* IFO 13534, *Escherichia coli* IFO 12734, *Klebsiella Pneumoniae* IFO 12009, *Pimelobacter simplex* IFO 12069, *Aspergillus ficuum* IFO 4034, *Beauveria bassiana* IFO 8554, *Calonectria hederae* IFO 30427, *Conichaetidium savoryi* IFO 30424, *Backusella circina* IFO 9231, *Cladobotryum apiculatum* IFO 7795, *Chloridium chlamydosporis* IFO 7070, *Corticium rolfsii* IFO 30071, *Cunninghamella echinulata* IFO 441, *Circinella simplex* IFO 6412, *Gliocladium deliquescens* IFO 6790, *Gliocephalotrichum cylindrosporum* IFO 9326, *Echinopodospora jamaicensis* IFO 30406, *Gelasinospora cerealis* IFO 6759, *Dichotomomyces cejpii* IFO 8396, *Pycnoporus coccineus* IFO 9768, *Neosartorya aurata* IFO 8783, *Penicillium janthinellum* IFO 4651, *Thamnostylum piriforme* IFO 6117, *Zygorhynchus moelleri* HUT 1305 and *Monascus ancha* IFO 5965.

4. A process for preparing optically active 3-chloro-1,2-propanediol, which comprises subjecting (R,S)-3-chloro-1,2-propanediol to the action of a microorganism capable of selectively metabolizing (R)-3-chloro-1,2-propanediol, wherein a compound having an SH group is added to the reaction solution, and collecting the residual (S)-3-chloro-1,2-propanediol and the microorganism is selected from the group consisting of *Pichia farinosa* IFO 1003, *Geotrichum fermentans* CBS 2264 and *Corynebacterium acetoacidophilum* ATCC 21476.

5. The process of claim 3, wherein the compound having an SH group is selected from the group consisting of dithiothreitol, dithioerythritol, glutathione, cysteine, mercaptoethanol, thioglycerol, 2,3-dimercaptopropanol, thioacetic acid, dimercaptosuccinic acid, 2-mercaptopropionic acid, 3-mercaptopropionic acid, thioglycollic acid, tert-butyl mercaptan, sodium hydrosulfide and potassium hydrosulfide.

6. The process of claim 4, wherein the compound having an SH group is selected from the group consisting of dithiothreitol, dithioerythritol, glutathione, cysteine, mercaptoethanol, thioglycerol, 2,3-dimercaptopropanol, thioacetic acid, dimercaptosuccinic acid, 2-mercaptopropionic acid, 3-mercaptopropionic acid, thioglycollic acid, tert-butyl mercaptan, sodium hydrosulfide and potassium hydrosulfide.

* * * * *